United States Patent
De Lima Perez Garcia et al.

(10) Patent No.: US 9,279,004 B2
(45) Date of Patent: Mar. 8, 2016

(54) SYNTHETIC PNTX(19) PEPTIDE, PHARMACEUTICAL COMPOSITIONS AND USE

(71) Applicant: UNIVERSIDADE FEDERAL DE MINAS GERAIS—UFMG, Belo Horizonte (BR)

(72) Inventors: Maria Elena De Lima Perez Garcia, Belo Horizonte (BR); Carolina Nunes Da Silva, Belo Horizonte (BR); Flávia De Marco Almeida, Belo Horizonte (BR); Rosangela Da Silva Lomeo, Belo Horizonte (BR); Paulo Sérgio Lacerda Beirão, Belo Horizonte (BR); Fernanda Silva Torres, Belo Horizonte (BR); Adriano Monteiro De Castro Pimenta, Belo Horizonte (BR)

(73) Assignee: UNIVERSIDADE FEDERAL DE MINAS GERAIS—UFMG, Belo Horizonte (BR)

(*) Notice: Subject to any disclaimer, the term of this patent is extended or adjusted under 35 U.S.C. 154(b) by 0 days.

(21) Appl. No.: 14/423,087

(22) PCT Filed: Aug. 20, 2013

(86) PCT No.: PCT/BR2013/000319
§ 371 (c)(1),
(2) Date: Mar. 19, 2015

(87) PCT Pub. No.: WO2014/028997
PCT Pub. Date: Feb. 27, 2014

(65) Prior Publication Data
US 2015/0218233 A1 Aug. 6, 2015

(30) Foreign Application Priority Data
Aug. 20, 2012 (BR) ............................ 102012020800
Aug. 13, 2013 (BR) ............................ 102013020574

(51) Int. Cl.
*A61K 38/00* (2006.01)
*A61K 38/10* (2006.01)
*C07K 7/08* (2006.01)
*C07K 14/435* (2006.01)

(52) U.S. Cl.
CPC ............ *C07K 14/43518* (2013.01); *A61K 38/10* (2013.01); *C07K 7/08* (2013.01); *A61K 38/00* (2013.01)

(58) Field of Classification Search
None
See application file for complete search history.

(56) References Cited

U.S. PATENT DOCUMENTS

2011/0236467 A1   9/2011   Perez Garcia et al.

FOREIGN PATENT DOCUMENTS

BR   PI0800596   9/2009

OTHER PUBLICATIONS

Nunes et al., Toxicon, 2008, 51, 1197-206.*
Int'l Search Report for PCT/BR2013/000319, seven pages, mailed Sep. 30, 2013.
Written Opinion for PCT/BR2013/000319, seven pages, mailed Sep. 30, 2013.
Andrade et al. "Penile erection induced in vivo by a purified toxin from the Brazilian spider *Phoneutria nigriventer*" *BJU Intl*, vol. 102, No. 7, pp. 835-837 (Jun. 2008).
Nunes et al. "Tx2-6 toxin of the *Phoneutria nigriventer* spider potentiates rat erectile function" *Toxicon*, vol. 51, No. 7, pp. 1197-206 (Feb. 2008).
Nunes et al. "Nitric oxide-induced vasorelaxation in response to PnTx2-6 toxin from *Phoneutria nigriventer* spider in rat cavernosal tissue" *J Sexual Med*, vol. 7, No. 12, pp. 3879-3888 (Aug. 2010).
Nunes et al. "Increased cavernosal relaxation by Phoneutria nigriventer toxin, PnTx2-6, via activation at NO/cGMP signaling" *Intl J Impotence Res*, vol. 24, No. 2, pp. 69-76 (Mar. 2012).
Nunes et al. "Erectile function is improved in aged rats by PnTx2-6, a toxin from *Phoneutria nigriventer* spider venom" *J Sexual Med*, vol. 9, No. 10, pp. 2574-2581 (Aug. 2012).
Nunes et al. "New insights on arthropod toxins that potentiate erectile function" *Toxicon*, vol. 69, pp. 152-159 (Apr. 2013).
Torres et al. "Functional expression of a recombinant toxin rPnTx2-6 active in erectile function in rat" *Toxicon*, vol. 56, No. 7, pp. 1172-1180 (Apr. 2010).
Villanova et al. "Erection inducted by Tx2-6 toxin of *Phoneutria nigriventer* spider: Expression profile of genes in the nitric oxide pathway of penile tissue of mice" *Toxicon*, vol. 54, No. 6, pp. 793-801 (Jun. 2009).

* cited by examiner

*Primary Examiner* — Karlheinz R Skowronek
*Assistant Examiner* — Roy Teller
(74) *Attorney, Agent, or Firm* — Nixon & Vanderhye PC

(57) ABSTRACT

The present invention relates to a synthetic peptide of 19 amino acids, called PnTx(19), constituted from the sequence of the native toxin PnTx2-6 of the Phoneutria nigriventer spider. It also relates to pharmaceutical compositions containing such a peptide and to the use thereof in the treatment of erectile dysfunction and/or in potentiating the erectile function.

7 Claims, 7 Drawing Sheets

SEQUENCE LISTING

<160> NUMBER OF SEQ ID NOS: 1

<210> SEQ ID NO 1
<211> LENGTH: 19
<212> TYPE: PRT
<213> ORGANISM: Artificial Sequence
<220> FEATURE:
<223> OTHER INFORMATION: synthetic peptide

<400> SEQUENCE: 1

Gly Glu Arg Arg Gln Tyr Phe Trp Ile Ala Trp Tyr Lys Leu Ala Asn
1               5                   10                  15

Ser Lys Lys

SYNTHETIC PNTX(19) PEPTIDE, PHARMACEUTICAL COMPOSITIONS AND USE

This application is the U.S. national phase of International Application No. PCT/BR2013/000319, filed 20 Aug. 2013, which designated the U.S. and claims priority to Brazilian Application No. 1020120208008, filed 20 Aug. 2012, and Brazilian Application No. 1020130205745, filed 13 Aug. 2013; the entire contents of each of which are hereby incorporated by reference.

The present invention relates to a synthetic polypeptide of 19 amino acids, called PnTx(19), constituted from the sequence of native toxin PnTx2-6 of the Phoneutria nigriventer spider. It also relates to pharmaceutical compositions containing such a peptide and to the use thereof in the treatment of erectile dysfunction and/or in potentiating the erectile function.

The venom of the Phoneutria nigriventer spider, popularly known as "aranha-armadeira" ("armed spider") is rich in bioactive polypeptides with different pharmacological effects, acting chiefly in ion channels and receptors. The predominant symptoms caused by its venom result from general hyper-excitability. Studies have demonstrated that the venom toxicity comes largely from the effects of the PhTx2 fraction (for review see: BROGES, M. H. et al. In: Animal Toxin: State of the Art. Perspectives in Health and Biotechnology. Maria Elena de Lima, Adriano Monteiro de Castro Pimenta, Marie France Martin-Eauclaire, Russolina Benedeta Zingali and Nerve Rochat (organizing committee), Belo Horizonte-MG. Editora UFMG. 800p. 2009, GOMEZ, M. V. et al. Cellular and Molecular Neurobiology, 22: 5/6, 2002). The toxin PnTx2-6 (MM 5.291.3 Da), published from this fraction, reproduces the symptomatic effects of the total fraction after intracerebral injection into mice (LE SUEUR, L. P. et al. Acta Neuropathol. 105, 125-134,2003). Its action may be attributed to the delay in the current of inactivation of the channels for sodium, having also effect on the activation, in some subtypes of these channels, displacing the activation to more negative potentials (MATATEL, A. et al. Biochemistry. 48 (14), 3078-3088, 2009; CASSOLI et al., personal communication, 2012). The effect of PnTx2 on the erectile function of rats was described before in the patent application P10800596, entitled "Método para a potencialização da função erétil atravees do use das composigoes farmaceuticas de toxina Tx2-6 da aranha Phoneutria nigriventer" (A method for potentiating the erectile function by using the pharmaceutical compositions of PnTx2-6 from the spider Phoneutria nigriventer), potentiates the erection in normotensive rats, restores the erectile function on hypertensive animals (DOCA-sal), and also in diabetic mice or old-age rats. (for review see: NUNES, K. P. et al. The Journal of Urology, 9(10):2574-81, 2012). These effects deserves to be mediated by the activation of the enzyme Nitric Oxide Synthase (NOS) and release of nitric acid (NO) (YONAMINE, C. M. et al. Toxicon 44, 169-172, 2004; NUNES et al., 2008, 2009). Besides, it is suggested that some genes involved in the pathway of nitric acid have their expression enhanced in the erectile tissue of mice after treatment with the toxin PnTx2-6 (VILLANOVA, F. E. et al. Toxicon. 54(6), 793-801, 2009).

Nitric oxide (NO), a product from the hydrolysis of L-arginine by nitric oxide synthase (NOS), is an essential mediator of the erection process [LEWIS, R. W. et al. A. Definitions, classification, and epidemiology of sexual dysfunction. In: Sexual Medicine. Sexual Dysfunction in Men and Women, Lue, T. F.; Basson, R.; Rosen, R.; Giuliano, F.; Khoury, S.; Montorsi, F., (Editores.) International for Sexual Medicine, Paris, p. 39-72, 2004]. After release thereof by the non-adrenergic-non-cholinergic nerves (NANC), nitrergic nerves and endothelial cells, NO spreads into the trabecular and vascular vicinity of the smooth muscle of the penis to stimulate the activity of the soluble cyclase guanylate (GCs), increasing the concentration of cyclic guanosine monophosphate (GMPc) (TODA, N. et al. Pharmacol. Ther. 106 (2), 233-266, 2005; PRIETO, D. Int. J. Impot. Res (20(1), 17-29, 2008). The formation of GMPc induces the decrease in the levels of intracellular calcium, leading to relaxation of the smooth muscle cells with a subsequent penile tumescence (TODA et al., 2005). Erection ends due to the hydrolysis of the GMPc by the enzyme phosphodisesterase type 5 ((IGNARRO, L. J. et al. Biochem Biophys Res Commun., 170, 843-50, 1990; RAJFER, J. et al. N. Engl. J. Med. 326(2), 90-94, 1992; LEE, M. R. J. Biol. Chem. 272, 5063-5068, 1997; BIVALACQUA, T. J. et al. Trends Pharmacol. Sci., 21 (12), 484-489, 2000). At present, the main pharmacotherapy used for erectile dysfunction is PDE-5 inhibitors such as sildenafil (Viagra), taladafil (Cialis® and vardenafil (Levitra®) (MORELAND, R. B et al. Trends Endocrinol. Metab. 10(3), 97-104, 1999; PRIVIERO, F. B. et al. Acta Pharmacol. Sinica 28(6), 751-755, 2007; LEITE, R. at al. Recent Pat. Cardiovasc. Drug Discov. 2(2), 119-132, 2007). However, PDE-5 inhibitors are not efficient in the treatment of patient with vascular diseases, where the production of NO is impaired. Thus, since the relaxing effect of the smooth muscle of the cavernous body induced by PnTx2-6 is independent from the inhibition of the enzyme PDE-5, this toxin enabling the production of medicaments effective for patients with erectile dysfunction who may not be treated by the presently available medicaments.

Another important effect of PnTx2-6 refers to the stimulation of the release of cerebrocortical synaptosome glutamate of rat [SILVA, 2012—personal communication—SILVA, C. N. Análise da liberação de L-glutamato de sinaptosomas de córtex cerebral de rato pela toxina PnTx2-6 da peconha da aranha armadeira (Phoneutria nigriventer) (Analysis of the release of L-glutamate of from the cerebral cortex of rats by the toxin PnTx2-6 of the venom of the armed spider (Phoneutria nigriventer)). Initial evaluation of the activity of the synthetic peptide (PnTx-19) in releasing glutamate and as a potentiator of the erectile function. Master dissertation to be presented on Aug. 31, 2012, at the Biochemistry and Immunology of the Unviersidade Federal de Minas Gerais. Belo Horizonte, Minas Gerais, p. 120, 2012]. Yonamine et al. (2005) found that iodized PnTx2-6 can penetrate the hematoencephalic barrier and thus could exert some effects directly on the CNS, which was confirmed by Nunes et al. 2010 (NUNES, K. P. et al. J. Sex Med. 7: 3879-88, 2010).

Glutamate (L-glutamate or L-glu) is the main and most abundant excitatory neurotransmitter of the CNS on mammalians. It exerts a crucial role in mechanisms underlying the synaptic plasticity, which are part of the physiological bas of behavioral processes such as cognition and memory. L-glu also performs relevant functions in the development of the nervous system like formation, remodeling, elimination of synapses, migration, proliferation, neuronal differentiation, and cell death ((PRYBYLOWSKI, K. et al. J. Biol. Chem. 279, 9673-6, 1994; MCKINNEY, R. A. Journal Physiology. 588 (1), 107-116, 2010; MANENT, J. B., REPRESA, A. The Neuroscientist, 13 (3), 268-279, 2007; SCHLETT, K. Current Topics Medicinal Chemistry. 6(10), 949-960, 2006; VECINO, E. et al. The International Journal of Developmental Biology. 48 (8-9), 965-974, 2004). Besides, glutamate can facilitate the penile erection by activating some cerebra areas that are involved in the control of erectile function line the paraventricular nucleus (PVN), the tegmented ventral area (VTA), the hippocampus, among others (ARGIOLAS, A., MELIS, M. R. Prog. Neurobiol. 47, 235-255, 1995; SONG, Y., RAJASEKARAN, M. Urology. 64(6), 1250-1254, 2004; MELIS, M. R., ARGIOLAS, A. Neuroscience and Biobehavioral Reviews 35, 939-955, 2011; UCCU, S. et al. Neuropharmacology. 61(1-2), 181-188, 2011).

It is probable that PnTx2-6 has action on this system in the brain, since the first tests for toxicity with this toxin were made via intracerebral injection, and it was found that it caused erection (for review see: NUNES et al., 2009). On the other hand, other in vivo tests carried out with the toxin aiming at the study of the potentiation of the erectile function were made with subcutaneous or intravenous injections, which resulted in positive responses (NUNES, 2008b, NUNES et al., 2008a). Besides, Yonamine et al., found that iodized PnTx2-6 can penetrate the hematoencephalic barrier and thus exert some effects directly on the CNS. Our group also showed that PnTx-6 marked by the technetium and injected peripherally, although it concentrates in the penis, also appears in a small amount in the nervous tissue, making one believe that at least a part thereof crosses the hematoencephalic barrier (NUNES et al., 2010a). Studies on the action of the toxin on the hematoencephalic barrier are in the initial phase, with a view to understand the possible entry of this toxin into the CNS. What is known is that the toxin PnTx2-6 injected by both peripheral and central routes is capable of inducing erection. One should verify the mechanisms by which this action takes place. The concrete result of the peripheral action of the toxin on the erection refers to the relaxation of slices of the cavernous body when the toxin is applied directly onto this in vitro preparation (NUNES et al. 2010a; 2010b; 2012).

Matavel et al. (2009), using molecular modeling tools, indicated a few amino acids of the PnTx2-6, in unknown epitope, which allegedly interacts with the channel for sodium. In this context, the chemical synthesis of a partial peptide sequence of the PnTx2-6 that embraces these amino acids opens new perspectives for structural and pharmacological characterizations of the interaction of the molecules with their receptors. Besides, the peptide synthesis, relatively simple and with possibility of high yield, might provide material necessary to the pharmacologic study on different tissues, overcoming the limitation observed with material obtained by purifying the venom or even by heterologous expression, which is difficult and expensive (MATAVEL, A. et al. Biochemistry 48(14), 3078-3088, 2009). Thus, in the present technology one has developed the modified synthetic peptide PnTx(19), which exhibits a short polypeptide chain of 19 amino acids, which enables one to obtain it easily for commercial purposes, providing the development of pharmaceutical compositions for use in the treatment of erectile dysfunction and/or in potentiating the erectile function. Besides, in the present technology it was demonstrated that this peptide induces release of glutamate in cerebrocortical synaptosomes of rats, stimulates the relaxation of slices of cavernous bodies of mice and rats, exhibits lower toxic effect with respect to the native toxin from which it is derived, and further does not exhibit cardiac toxicity, unlike Viagra present on the market. It is also effective in hypertensive animals and exhibits low immunogenicity.

In the prior art, there are new formulations based on polypeptides derived from spider venom, as disclosed in application WO2009083808, entitled "COM POSITINS AND METHODS FOR TREATING ERECTILE DYSFUNCTION", which describes compositions comprising a polypeptide isolated from the venom of the black-widow spider (Latrodectus mactans) and biologically active fragments thereof. However, one did not find any peptide similar to that of the present invention for the treatment of erectile dysfunction.

DETAILED DESCRIPTION OF THE TECHNOLOGY

The present invention comprises the peptide PnTx(19), NH3-GERRQYFWIAWYKLANSKK-COOH (SEQ ID NO. 1), synthetized chemically by using the Fmoc/t-butyl strategy of synthesis on solid support (MERRIFIELD, R. B. Solid-phase peptide synthesis. Adv. Enzymol. Relat. Areas Mol. Biol. (32), 221-296, 1969). The peptide has 19 amino acid residues, is linear and was designed from the probable three-dimensional structure of the PnTx2-6 proposed after analysis for bioinformatics and molecular modeling studies. This embraces the hydrophobic "core" and the positively charted residues that surround this region, which, according to the molecular modeling studies, are responsible for the interaction of the toxin with the channel for sodium (MATAVEL et al., 2009). The sequence (discontinuous epitope) developed from these molecular modeling studies underwent crucial modifications in the present invention, so that its activity in the erectile function could be kept: the amino acid cysteine, at position 17, was replace by serine, and the peptide was amidated on the C-terminal portion and acetylated in the N-terminal portion, with a view of increasing the solubility thereof.

Figure 4:
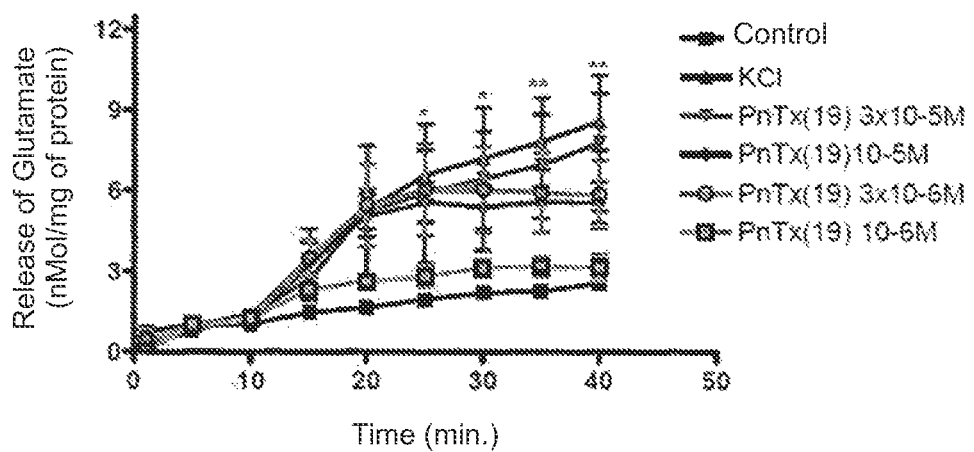
FIG. 4—Effect of different concentrations of the PnTx(19) in releasing L-glutamate—ELISA Plate containing 300 μl/well of the synaptosome mixture (10% final volume) and NADP+(final concentration of 1 mM) in KRH with calcium (2 mM), kept at 37° C. under constant stirring was monitored. One carried out the reading of the fluorescence on the spectrofluorimeter for 2460 seconds. The enzyme GDH (35 units for the final volume of 300 μl) was added to the wells at 60 seconds; at 660 seconds, in different wells, one added different concentrations of PnTx(19) ("$10^{-5}$M, $3 \times 10^{-5}$ M, $10^{-6}$ M and $3 \times 10^{-6}$ M") and the KCI (33 mM). As negative controls, one used wells containing untreated synaptosomes with the toxin. The results exhibit the average and the standard error of two independent experiments, carried out in triplicate. * $P<0.05$ represent the levels of significance of assays compared with the control—represented by the untreated synaptosomes.

The tests for activity demonstrated that PNTx(19), just as PnTx2-6, interferes with the glutamatergic system in cerebrocortical synaptosomes of rats. Different concentrations of the peptide were used, and it was found that, in the dose of $3 \times 10^{-5}$M, PnTx(19) induced an increase in the release of glutamate in cerebrocortical synaptosomes of rats (FIG. 4).

Figure 5:
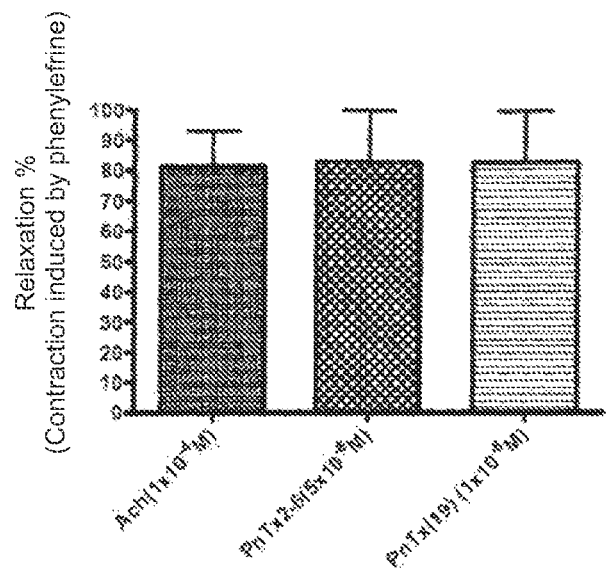
FIG. 5—Effects of the toxin PnTx2-6 and of the peptide PnTx(19) ($1 \times 10^{-6}$M) on the relaxation of strips of cavernous goodies of mice. The strips were pre-contracted with phenylefrine ($10^{-5}$ M) and relaxed with acetylcholine ($10^{-4}$M)-control, PnTx2-6 ($5 \times 10^{-8}$M) and PnTx(19) ($\times 10^{-6}$ M) (n=3).

The action of the peptide in the erection was verified by using strips of cavernous body isolated from mice. 1 µM PnTx(19) provided significant relaxation of the cavernous-body strip of mice, approximately 80% (FIG. 5), an action similar to that evoked by 50 nM of PnTx2-6 and 100 µM of acetylcholine. Probably, the relaxation of the cavernous body is due to the connection of the linear peptide to the channels for sodium in the cavernous body, triggering the subsequent events in the erection route.

The development of the synthetic peptide PnTx(19) enables one to obtain the highest amounts of the active molecule with the possibility of decreasing the toxic effects with respect to the native toxin PnTx2-6, which provides the development of pharmaceutical compositions for the treatment of erectile dysfunction and/or in potentiating the erectile function.

Such pharmaceutical compositions are characterized by comprising a synthetic peptide and an excipient or a mixture of pharmaceutically acceptable excipients, wherein the peptide may be present either in the free from or coupled to controlled release systems. The controlled release systems may include lyposomes, cyclodextrines, biodegradable polymers, capsules, micro- and nano-capsules, micro- and nano-particles, bolus preparations, osmotic pumps, diffusion devices, lypospheres, transdermal administration systems and/or liquids that, when subjected to changes in temperature, form a solid or a gel in situ. In this way, the pharmaceutical compositions may be administered by the oral, topical, intramuscular, intravenous, subcutaneous, inhalation routes, or by implantable devices.

The present invention can be better understood with reference to the following examples, which are no limitative of the technology.

Example 1

Chemical Synthesis in Solid Phase and Purification of the Peptide PnTx(19)

The synthetic peptide called PnTx(19) (NH3-GlyGluArgArgGlnTyrPheTrp IleAlaTrpTyrLysLeuAlaAsnSerLysLys-OOOH) was partially designed by using the bioinformatics program PEPOP. In this way, one proposed a discontinuous epitope containing 19 amino acids for the toxin PnTx2-6 (FLEURY, Cécile, Bioinformatics tools dedicated to the study of the structure-function-antigenicity relationship in animal peptide toxins. Doctoral thesis, Department of Biochemistry and Immunology of the Unviersidade Federal de Minas Gerais, Belo Horizonte, MG, 180 p., 2009).

With a view to increasing the solubility of the peptide, in the present technology one has synthetized the PnTx(19) with modifications in the N-terminal portion (acetylation) and C-terminal portion (amidation). The acetylated and amidated peptide PnTx(19) proved to be water-soluble.

Figure 1:
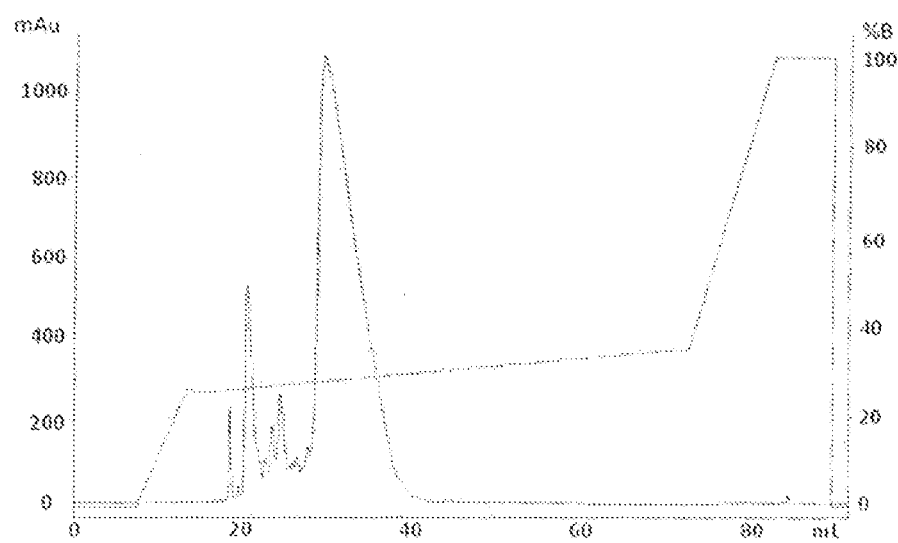
FIG. 1—Reversed phase chromatography in HPLC system of the products of the synthesis of the peptide PnTx(19). Preparatory column Sphasil peptide C8 5μ ST 4.6/100, balanced with water Milli-Q 0.1% TFA (by volume) eluted with a gradient 0 to 25% solution B (0.1% TFA/acetonitrile v/v) in 3 minutes, 25 to 35% of B in 30 minutes and 35 to 100% of solution B in 5 minutes, at a flow rate of 2.0 ml/minute.
Figure 2:
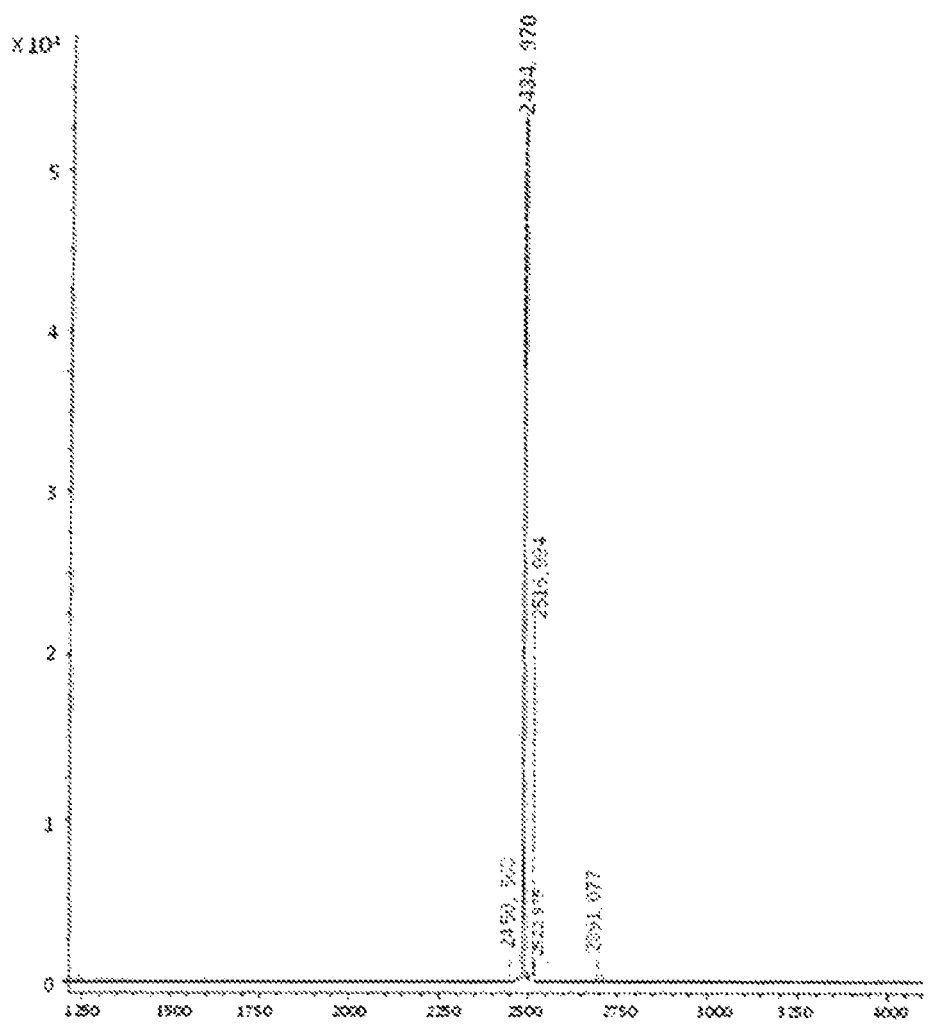
FIG. 2—Mass spectrometry of the fraction containing the synthetic peptide PnTx(19). The molecular mass of the PnTx (19) of 2484.9 Da was determined by MALDI-TOF.

The peptide PnTx(19) was purified by reversed-phase chromatography (HPLC ÄKTA Explorer 10). The chromatographic profile presented in FIG. 1 demonstrates the presence of synthesis by-products and the fraction referring to the PnTx(19), which elutes with 29% buffer B. After purification, the analysis by mass spectrometry (MALDI-TOF) showed only a group of molecular species in the spectrum, the molecular mass of which was of 2484.970 Da (FIG. 2), compatible with the mass expected for the peptide PnTx(19).

Example 2

Test for Synoptosomal Viability

Adult rats (240-300 g) were decapitated the brains were rapidly removed, immersed into homogenization solution (sucrose 0.32 M, EDTA 1 Mm and Dithiotreitol (DTT) 0.25 mM, pH=7.4) and kept in ice, then they were used in preparing the synaptosomes, as previously described by Dunkley et al 1988 (DUNKLEY, P. R.; Brain Research, 441, 59-71, 1988).

As control of the viability of the synaptosomes and also for verifying a possible lytic activity of the peptide, one carried out tests for activity of the enzyme lactate dehydrogenase, according to Kubowistz, Ott, 1943 (KUBOWISTZ, F., OTT, C. Biochem Z. 319, 94-117, 1943).

Figure 3:
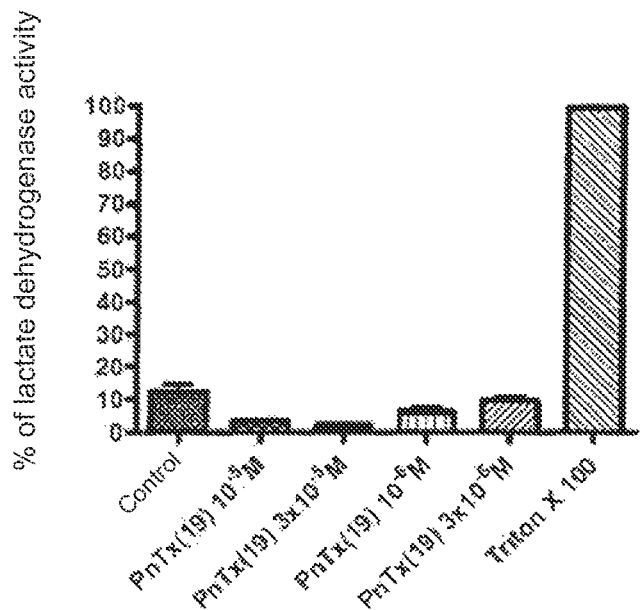
FIG. 3—Synaptosomal viability—verified by the activity of the enzyme lactate dehydrogenase, which oxidizes the NADH to NAD+. The latter determines a reduction in the reading (339 nm), which enables one to qualify the enzymatic activity. The reaction mixture was incubated for 60 min with PnTx(19) ($10^{-5}$ M; $3 \times 10^{-5}$ M; $10^{-6}$ M; $3 \times 10^{-6}$ M) and the activity percentage evaluated with respect to the lysis triggered by the Triton X-100, considered=100% of lysis. The activity of this enzyme is proportional to the breakage of the synaptosomes, considering that this is an enzyme of the intracellular compartment.

The LDH activity was evaluated in control conditions, in the presence of 1% Triton X-100 (100% of lysis) and in the presence of PnTx(19) in the following concentrations $10^{-5}$ M; $3 \times 10^{-5}$ M; $10^{-6}$ M; $3. \times 10^{-6}$ M. The results of FIG. 3 demonstrate that the peptide does not affect the synaptosomal viability and/or exocytotic machinery, since the values obtained were 3.4% of lysis for the concentration $10^{-5}$ M; 2% of lysis for the concentration $3 \times 10^{-5}$ M; 6% of lysis for the concentration $10^{-6}$ M; 9% of lysis for the concentration of $3 \times 10^{-6}$ M, values comparable with the control (absence of the peptide).

Example 3

Effects of the Toxin PnTx2-6 and of the Peptide PnTx(19) in Cavernous-Body Strips of Mice Mice were sacrificed by decapitation, their penis were removed surgically and placed on a Petri dish containing Krebs Ringer bicarbonate—(NaCl, 118.1; KCl, 4.7; KH2PO4, 1.0; MgSo4, 1.0: NaHCO3, 25.0; CaCl2, 2.55; and Glucose, 11.1 mM), bubbled with a mixture of 95% O2 and 5% CO2. The gland, the spongy body and the urethra were removed and the cavernous bodies were desiccated with removal of the tunica albuginea and separated by cutting the fibrous septum between them. The strips of cavernous bodies measuring about 1×1×7 mm were mounted separately in a chamber, one end thereof being secured to an electrode and the other linked to a transducer. The chambers contained Krebs (pH 7.4) at 37 C, balanced with 95% O2 and 5% CO2.

The tissue was stretched by a passive force of 2.0 mN and stabilized for 60 minutes, the solution being replaced every 15 minutes. The changes in isometric force were recorded by using an isometric force transducer (World Precision Instruments, Inc., Sarasota, Fla., USA), connected to an amplifier (TBM-4 model; World Precision Instruments, Inc., USA), using software WinDaq Data Acquisition (Dada® Instruments, USA). For evaluating the contractile capability of the preparations, a KCl solution (120 mM) was added to the slices of cavernous bodies and then the preparation was washed with Krebs three times.

The slices of cavernous body were pre-contracted with phenylfrin (100-5 M) and the relaxation was evoked by acetylcholine 10-4M (control), PntX2-6 (5×10-6M) and the peptide PnTx(19) (1×10-6M).

FIG. 4 shows that the toxin PnTx2-6 (5×10-8 M) and the peptide PnTx(19) (10-6 M) induce relaxation of 83%, while the control with acetylcholine (10-4 M) induced 81.6% of relaxation on strips of cavernous bodies of mice pre-contracted by phenylfrin (10-5 M). These results indicate that both the toxin PnTx2-6 and the peptide PnTx(19) are active in relaxing slices of cavernous bodies of mice.

Example 4

Effect of the Synthetic Peptide PnTx(19) in Releasing L-glutamate

The release of L-glutamate was analyzed according to the proposal of Nicholls et al. 1987 (NICHOLLS, D. et al. J. Neurochem. 49, 5057, 1987). In order to evaluate whether the peptide was capable of inducing release of L-glutamate in cerebrocortical synaptosomes of rats, just as the native toxin, one analyzed the effect thereof at the following concentrations: 10-5M, 3×10-5M, 10-6M, and 2×10-6 M, FIG. 5.

From these results one observes that, in the experimental conditions, only at the concentration of 3×10-5M the peptide was capable of inducing significant release of L-glutamate, when compared with the control (absence of PnTx19).

Example 5

Effects of the Peptide PnTx-19 on the Heart

Effect on the Sodium Current

Figure 6:
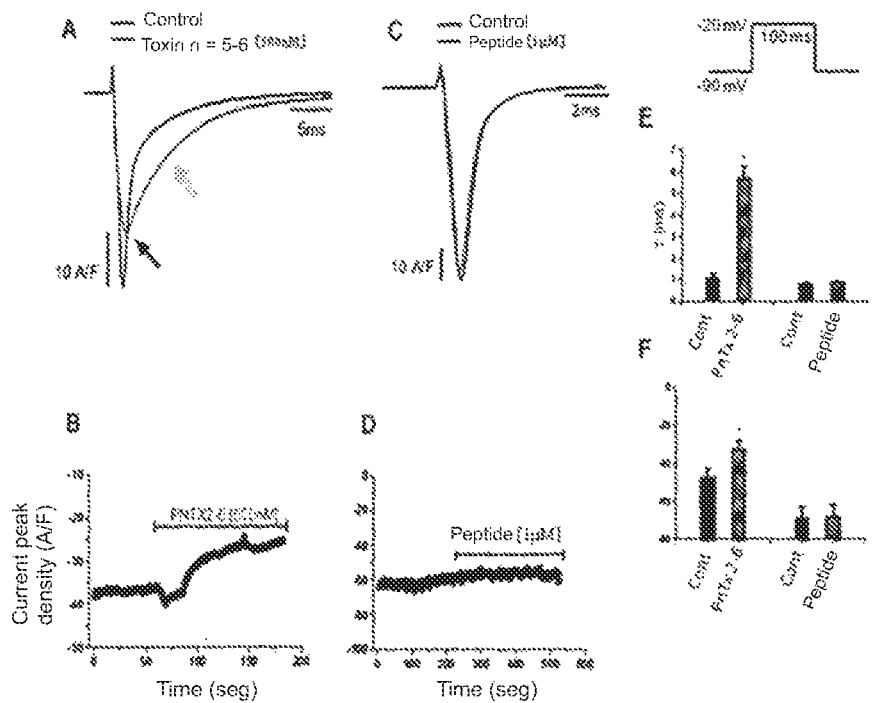
FIG. 6—Effects of the peptide PnTx-19 and of the toxin PnTx2-6 in the cardiac sodium current. A—Effect of the toxin PnTx2-6 on the peak of sodium current (black arrow) and in the inactivation current (gray arrow). C—Effect of the peptide PnTx-19 on the peak of the sodium current and in the inactivation current. D—Course of time of peak in the sodium current, during the perfusion of PnTx-19 and PnTx-26. Each black circle indicates the amplitude of the Ina, measured every 1 second in a membrane potential of −20 mV. The gray bars indicate the moment when the cell was exposed to PnTx2-6 or PnTX-19 (peptide). The bar graphs summarize the effects of PnTx2-6 500 nM (n=7) and of the peptide PnTx-19 (peptide) 1 μM (n=12) in the decay constant (E) and reduction of the sodium current (F). Bars indicate average±SEM, *p<0.05 with respect to the controls.

Patch-clamp experiments were carried out with a view to analyze the effects of the toxin PnTx2-6 and of the peptide PnTx-19 on channels for sodium Nav1.5, present in cardiomyocytes. Records evidenced that the toxin PnTx2-6 causes a decrease in the peak of sodium current, delaying the inactivation current. These effects were not observed for PnTx-19 (FIGS. 6 A and C). In FIG. 6 B one observes that PnTx2-6 promoted a reduction of the density of the sodium current, and this phenomenon was not observed in the presence of the peptide either (FIG. 6 D).

Effect on the Ventricular Pressure, Heart Rate and Derivative±dP/dt

Figure 7:
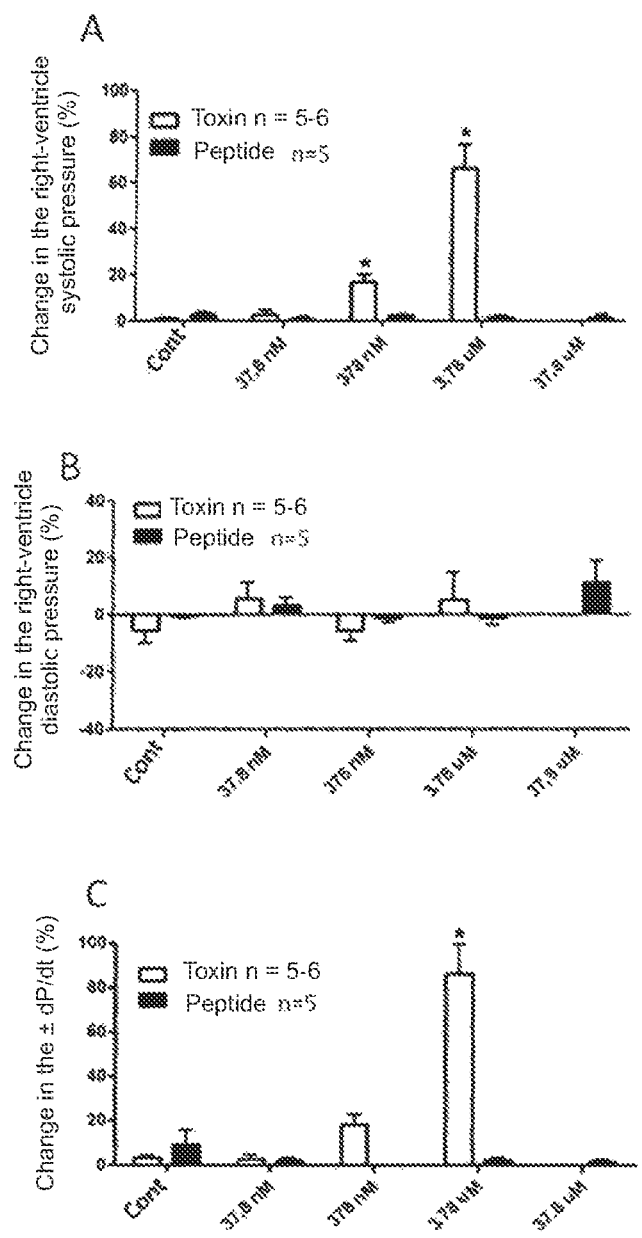
FIG. 7—Response dose curve of the peptide PnTx-19 and of the Toxin PnTx2-6 in the right (A) and (B) ventricular pressure, derived±dP/dt (C and D) and cardiac rate (E) of rats.
Figure 7:
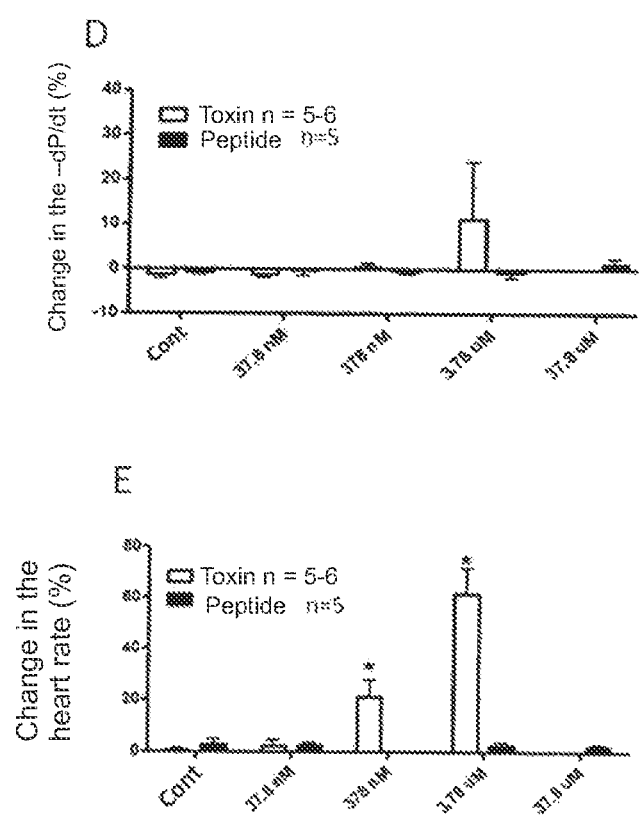

The rats were kept under a controlled cycle of 12 h light/darkness at a stable temperature with free access to water and food. They were decapitated 10 to 15 minutes after intraperitoneal injection of Heparin (200 IU). The thorax was opened, the heart was carefully desiccated and perfused through an aortic tip with Krebs-Ringer solution (KRS) containing (by mmol/L) NaCl (118.4), KCl (4.7), KH2PO4 (1.2), MgSO4.7H2O (1.2), CaCl2.2H2O (1.25), glucose (11.7) and NaHCO3 (26.5). The perfusion flow was kept constant (10 mL/min) at 37° C. and under constant oxygenation (5% CO2 and 95% O2). A balloon connected to a pressure transducer was inserted into the right ventricle, and one monitored the ventricular pressure, heart rate and derivative±dP/dt (FIG. 7). The balloon volume was adjusted to a final diastolic pressure of about 10 mm Hg. After a period for reaching the balance (30 to 40 minutes), 100 μmol/L carrier were injected (control), toxin at concentrations of 37.8 nmol/L-3.78 μmol/L or a peptide at concentrations of 37.8 nmol/L-37.8 μmol/L in perfusion buffer.

As shown in FIG. 7, the toxin induced an increase dependent upon the concentration, under the final right ventricle systolic pressure (RFVSP/PVSFD) and in the +dP/dt, AND −dp/dt, at most by 66.7±13.55%, and 61.6±9.89%, respectively (FIG. 7A; C and D). However, the toxin did not alter the final diastolic pressure and the heart rate. In contrast, the peptide did not alter any of these parameters, even at high concentrations (FIGS. 7 B and E).

The results are the average±SEM. Analyses of the one-way variance (ANOVA), followed by the Newman-Keuks posttest were used to analyze the parameters on isolated hearts. For statistical analyses p<0.05 was considered.

Example 6

Immunogenicity of the Peptide PnTx-19

Figure 8:
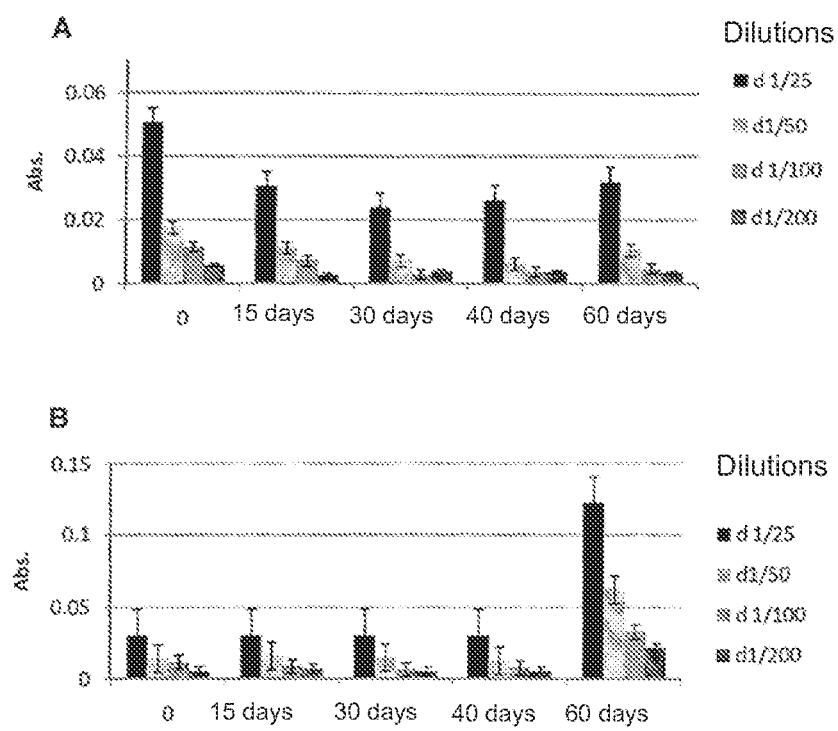
FIG. 8—Analysis of the antibody titer. A) Control: adjuvant (aluminum hydroxide). B) antibody titer after administration of the peptide PnTx-19 (10 µG) in different days.

Swiss, male, 20-23 gram mice were divided into 2 groups (Control—Adjuvant: aluminum hydroxide—FIG. 8 A and PnTx-19-10 μG—FIG. 8B), each group containing 4 animals. The mice were immunized by subcutaneous route. 21, 35 and 49 days from the first inoculation, the mice received a reinforcement of the above-mentioned preparations. To verify the presence of antibodies against the PnTx-19, the serum collected from the mouse tails was evaluated 15, 30, 40 and 60 days after the first inoculation through the indirect immunoenzymatic assay (ELISA), as described for other preparations (DEL PINO, F. A. B., BRANDELLI, A., GONZALES, J. C., HENRIQUES, J. A. P., DEWES, H., Effect of antibodies against β-N-acetylglucosaminidase on reproductive efficiency of the bovine tick Boophilus microplus. Vet. Parasitol. 79, 247-255, 1998).

The immunogenicity of PnTx19 was evaluated after subcutaneous injection of 10 μg thereof (FIG. 8B). No hypersensitivity or death reactions of the animals were observed during the assays. One found a minor increase in the titer of the antibodies in group 2 (PnTx-19-10 μg) 60 days after the first inoculation of the peptide (FIG. 8B). It is important to point out that the dose of peptide of 10 μg is about 12.5 times as high as the DL50 estimated for toxin PnTx2-6 (0.79 μg/mouse) (CORDEIRO M. N., DINIZ C. R., VALENTIM A. C., VON EICKSTEDT, GILROY J., RICHARDSON M. The purification and amino acid sequences of four Tx2 neurotoxins from the venom of the Brazilian 'armed' spider Phoneutria nigriventer (Keys). FEBS Lett. 310, 153-156, 1992).

The invention claimed is:

1. A synthetic peptide of comprising the sequence GERRQYFWIAWYKLANSKK (SEQ ID NO: 1).

2. The synthetic peptide of claim 1, wherein the peptide comprises modifications of acetylation and amidation.

3. A method of using the synthetic peptide of claim 1, comprising administering the synthetic peptide to a subject affected by erectile dysfunction and/or for potentiating erectile function.

4. A pharmaceutical composition comprising the synthetic peptide of claim 1, and an excipient or a mixture of pharmaceutically acceptable excipients.

5. The pharmaceutical composition of claim 4, wherein the peptide is present in free form or coupled to a controlled release system selected from the group consisting of lyposomes, cyclodextrins, biodegradable polymers, capsules, micro- and nanocapsules, micro- and nanoparticles, bolus preparation, osmotic pumps, diffusion devices, lypospheres, transdermal administration systems, liquids that, when subjected to changes in temperature, form a solid or a gel in situ, and combinations thereof.

6. The pharmaceutical composition of claim 4, which is administered by an oral, topical, intramuscular, intravenous, subcutaneous, or inhalation route, or by an implantable device.

7. A method of treating erectile dysfunction, comprising administering the synthetic peptide of claim 1 to an individual affected by erectile dysfunction and/or for potentiating erectile function.

* * * * *